(12) United States Patent
Heriot

(10) Patent No.: US 10,736,775 B2
(45) Date of Patent: Aug. 11, 2020

(54) METHOD AND DEVICE FOR TREATING RETINAL DETACHMENT

(71) Applicant: Wilson J. Heriot, Malvern (AU)

(72) Inventor: Wilson J. Heriot, Malvern (AU)

(73) Assignee: Heriot Eyecare Pty Ltd., Melbourne (AU)

( * ) Notice: Subject to any disclaimer, the term of this patent is extended or adjusted under 35 U.S.C. 154(b) by 974 days.

(21) Appl. No.: 14/799,330

(22) Filed: Jul. 14, 2015

(65) Prior Publication Data

US 2016/0008170 A1 Jan. 14, 2016

Related U.S. Application Data

(63) Continuation of application No. PCT/AU2014/000023, filed on Jan. 15, 2014.

(30) Foreign Application Priority Data

Jan. 15, 2013 (AU) .............................. 20133900144

(51) Int. Cl.
*A61F 9/007* (2006.01)
*A61F 9/008* (2006.01)
(Continued)

(52) U.S. Cl.
CPC .......... *A61F 9/00727* (2013.01); *A61B 18/04* (2013.01); *A61F 9/00821* (2013.01); *A61B 2018/00321* (2013.01); *A61B 2018/00619* (2013.01); *A61B 2018/00642* (2013.01); *A61B 2018/00714* (2013.01);
(Continued)

(58) Field of Classification Search
CPC ...... A61F 9/007; A61F 9/00727; A61F 9/008; A61F 9/00821; A61F 9/00861; A61F 9/00863; A61B 18/04; A61B 2018/044; A61B 2018/046; A61B 2018/048;
(Continued)

(56) References Cited

U.S. PATENT DOCUMENTS 4,359,049 A 11/1982 Redl et al. .................. 128/218
5,997,498 A * 12/1999 de Juan, Jr. ......... A61F 9/00821
604/24

(Continued)

OTHER PUBLICATIONS

International Preliminary Report on Patentability (Chapter I), dated Jul. 21, 2015, for PCT/AU2014/000023, pp. 1-8.
(Continued)

*Primary Examiner* — Ahmed M Farah
(74) *Attorney, Agent, or Firm* — J. Peter Paredes; Rosenbaum IP, P.C.

(57) ABSTRACT

A device for fusing two or more tissues is disclosed. The device comprises a hand held probe comprising a fluid receiving opening, a channel and an outlet in fluid communication whereby fluid passes through the channel and exits the outlet where it is directed to at least one of the two or more tissues and/or a space in-between. A disruptive emitter comprised on the probe which emits a force sufficient to fuse the two or more tissues. The device finds particular application to treatment of a detached retina by fusing the retina and the retinal pigmented epithelium. A method of fusing two or more tissues including a retina and underlying retinal pigmented epithelium is also disclosed.

7 Claims, 6 Drawing Sheets

(51) Int. Cl.
*A61B 18/04* (2006.01)
*A61B 18/00* (2006.01)

(52) U.S. Cl.
CPC ... *A61B 2018/044* (2013.01); *A61B 2218/002* (2013.01); *A61F 2009/00863* (2013.01)

(58) Field of Classification Search
CPC .......... A61B 2018/00619; A61B 2018/00636; A61B 2018/0064; A61B 2018/00714
USPC ...... 606/4, 6, 10–16, 27, 28; 607/88, 89, 92, 607/96, 100, 102–105; 128/898
See application file for complete search history.

(56) References Cited

U.S. PATENT DOCUMENTS

| | | | | |
|---|---|---|---|---|
| 6,309,374 | B1* | 10/2001 | Hecker | A61F 9/007 604/117 |
| 6,607,522 | B1 | 8/2003 | Hamblin et al. | 606/8 |
| 7,349,589 | B2* | 3/2008 | Temelkuran | A61B 1/0017 385/11 |
| 8,986,242 | B2* | 3/2015 | Auld | A61M 5/31553 604/24 |
| 2001/0029335 | A1* | 10/2001 | Juan, Jr. | A61B 5/6848 600/437 |
| 2002/0082667 | A1 | 6/2002 | Shadduck | 607/96 |
| 2004/0039253 | A1* | 2/2004 | Peyman | A61F 9/00727 600/201 |
| 2004/0073231 | A1* | 4/2004 | Juan, Jr. | A61F 9/007 606/108 |
| 2005/0154384 | A1 | 7/2005 | Ben-Nun | 606/29 |
| 2007/0239260 | A1 | 10/2007 | Palanker et al. | 623/1.15 |
| 2009/0149846 | A1* | 6/2009 | Hoey | A61B 17/42 606/27 |
| 2009/0254023 | A1* | 10/2009 | Akduman | A61F 9/0017 604/60 |
| 2009/0312749 | A1* | 12/2009 | Pini | A61F 9/00736 606/4 |
| 2011/0060320 | A1* | 3/2011 | Aharon-Attar | A61F 9/00727 606/4 |
| 2019/0343681 | A1* | 11/2019 | Heriot | A61F 9/00727 |

OTHER PUBLICATIONS

Jelínková et al., "Diode-Pumped Tm:YAP Laser for Eye Microsurgery", Proceedings of SPIE—The International Society for Optical Engineering, vol. 6871 68712N-2, pp. 1-8, Mar. 2008.
Examination Report No. 1 issued in foreign application, Au 2014207245, pp. 1-6 (dated Nov. 23, 2017).

* cited by examiner

METHOD AND DEVICE FOR TREATING RETINAL DETACHMENT

CROSS-REFERENCE TO RELATED APPLICATIONS

The present application claims priority from and is a continuation of PCT Application No. PCT/AU2014/000023, filed Jan. 15, 2014, which claims priority from Australian Patent Application No. 2013900144, filed Jan. 15, 2013, each of which is incorporated herein by reference in their entirety.

BACKGROUND

The invention described herein relates generally to a method and device for treating tissue detachment which uses direct fusion. In particular, the invention is directed to a method and device for treating tissue detachment such as retinal detachment, the method reduces or eliminates the reliance on wound healing and reduces the potentially detrimental inflammatory response, although the scope of the invention is not necessarily limited thereto.

Tissues sometimes detach from each other due to injury or other pathology. One example is retinal detachment, a disorder in which the retina peels away from its underlying layer of support tissue. Initial detachment may be localized, but without rapid treatment the entire retina may detach, leading to vision loss and blindness.

The role of a peripheral retinal tear in the causation of rhegmatogenous retinal detachment (RRD) was popularised by Jules Gonin in 1904. Gonin subsequently developed the first successful technique for retinal detachment repair utilising a white hot metal probe passed through a scleral incision. The thermal injury of the retina and adjacent retinal pigment epithelium (RPE) and choroid formed a watertight barrier between the subretinal space and the vitreous cavity. Thermal injury remains the basis for all retinal detachment repair, ranging from the historic hot metal probe to penetrating diathermy, and now contemporary cryo-retinopexy and laser treatment.

Traditional retinal detachment repair utilizes wound healing to create new (granulation) tissue to obliterate the subretinal space to seal the retinal tear margins. Laser or cryoretinopexy creates inflammation of both the retina and RPE. Scleral buckling or tamponade with gas or silicone oil "clamps" both injured tissues together while the wound heals. An improved technique of retinal repair is required.

SUMMARY OF THE INVENTION

Provided herein are systems, methods and devices for fusing two or more tissues comprising: a hand held probe comprising a fluid receiving opening, a channel and a fluid outlet in fluid communication whereby fluid received in the opening passes through the channel and exits the outlet where it is directed to at least one of the two or more tissues and/or a space in-between; and a disruptive emitter comprised on the hand held probe which emits a force to be directed to at least one of the two or more tissues sufficient to fuse the two or more tissues.

A device for treating a detached retina is also disclosed and comprises: a fluid pump to provide a sterile, temperature-regulated desiccating fluid flow; and a probe comprising an outlet for the sterile, temperature-regulated desiccating fluid flow whereby the sterile, temperature-regulated desiccating fluid exiting the outlet to be directed to at least one of the two or more tissues and/or to a gap between the two or more tissues to dehydrate at least one of the two or more tissues and/or the gap.

A method for fusing two or more tissues is disclosed, the method comprising: providing a sterile, temperature-regulated desiccating fluid flow which exits out of a probe so that the sterile, temperature-regulated fluid flows to at least one of the two or more tissues and/or to a gap between the two or more tissues; and directing a disruptive emission to at least one of the two or more tissues and/or the gap sufficient to fuse the two or more tissues.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In order that the present invention may be readily understood and put into practical effect, reference will now be made to the accompanying illustrations, wherein like reference numerals refer to like features.

DETAILED DESCRIPTION OF THE INVENTION

Figure 1:
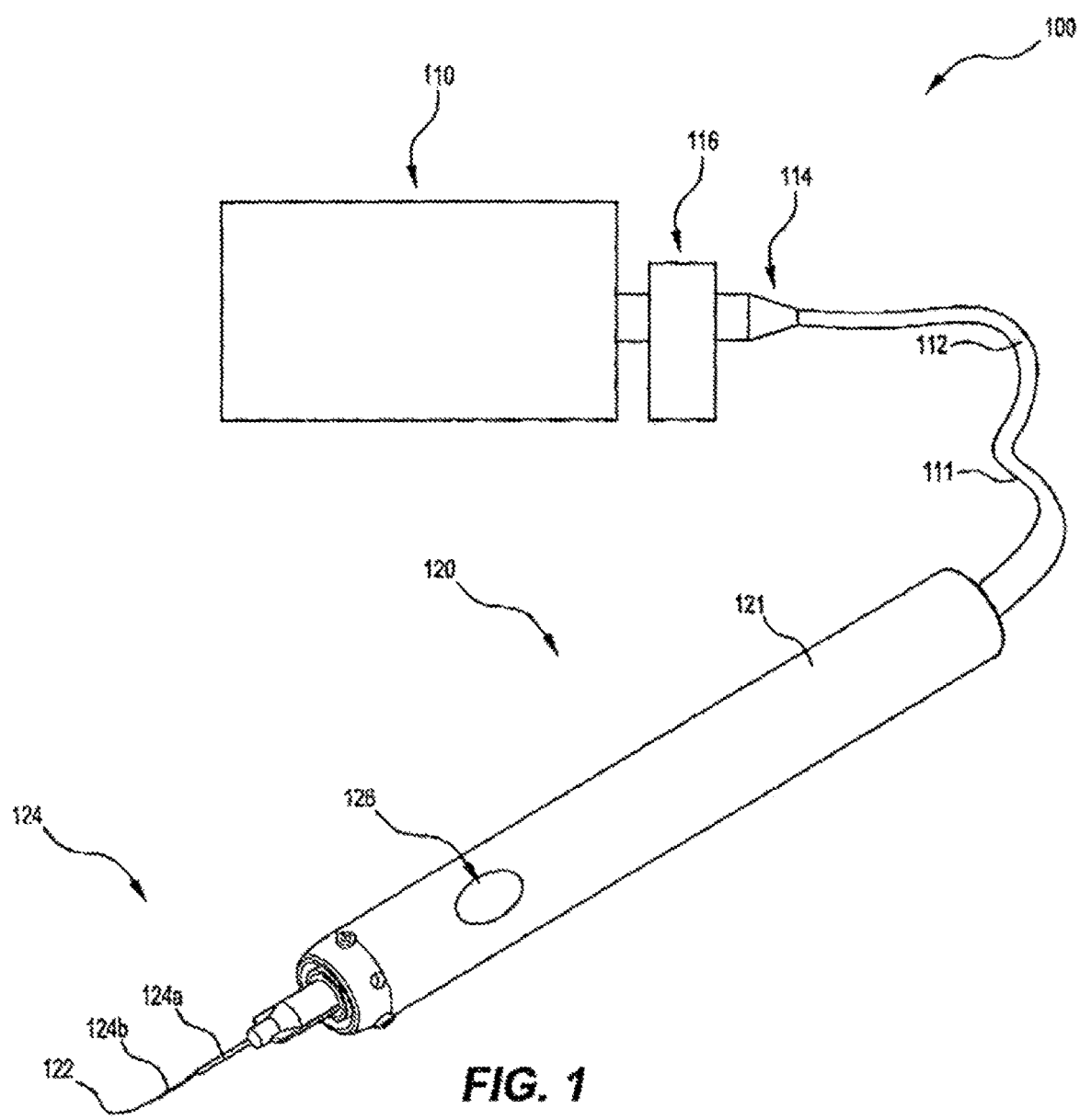
FIG. 1: shows one embodiment of a device according to the invention.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

The present inventor has discovered a novel and inventive method and device for fusing two or more tissues which has particular application to the repair of a detached retina. Existing methods and devices for treating retinal detachment are primarily aimed at creating a tissue injury to deliberately invoke an inflammatory response and wound healing and/or scar tissue formation to seal the retinal tear margin. In one embodiment, the present invention has arisen after the present inventor discovered a method and device for treating retinal detachment which seals the margin by directly fusing both layers together as the primary event. This minimizes, or at least reduces, tissue injury and reduces or eliminates the therapeutic role of the inflammatory response.

In one aspect, there is provided a device for fusing two or more tissues comprising: a hand held probe comprising a fluid receiving opening, a channel and a fluid outlet in fluid communication whereby fluid received in the opening passes through the channel and exits the outlet where it is directed to at least one of the two or more tissues and/or a space in-between; and a disruptive emitter comprised on the hand held probe which emits a force to be directed to at least one of the two or more tissues sufficient to fuse the two or more tissues.

In one embodiment of the first aspect, the disruptive emitter comprises a fusion-causing emitter.

In another embodiment of the first aspect, the disruptive emitter comprises a thermal emitter or a light emitter. The thermal emitter may comprise a heat emitter or a cold emitter. The light emitter may comprise a laser fibre and a laser fibre tip.

In yet another embodiment of the first aspect, the thermal emitter comprises a heating element disposed inside the channel for heating the fluid so that fluid exiting the outlet comprises a temperature sufficient to fuse the two or more tissues.

According to the first aspect, the heating element may be located at a proximal end of the probe to minimise any offset in temperature before fluid exits the outlet.

According to the first aspect, the heating element may comprise a coil. The coil may be comprised of a nichrome wire.

According to the first aspect, the thermal emitter may heat the fluid to a temperature so that the exiting fluid may comprise a temperature in the range of 55-100° C.; 55-80° C.; 60-75° C.; or 62-70° C. to thermally fuse the two or more tissues. The thermal emitter may heat the fluid to a temperature of 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100° C.

In another embodiment of the first aspect, the disruptive emitter comprises a blind tip of a laser fibre.

In still another embodiment of the first aspect, the light emitter comprises a laser fibre disposed on the hand held probe which emits laser light sufficient to fuse the two or more tissues.

In a preferred embodiment of the first aspect, the device is a device for treating or when used to treat a detached retina and/or the probe is an intraocular probe.

According to one embodiment of the first aspect, the device may further comprise a detachable tip which may be joined in fluid communication with the hand held probe to allow passage of the fluid from the hand held probe to the detachable tip so that fluid exits out of the detachable tip.

In another embodiment of the first aspect, the hand held probe may comprise an orifice along a length of the probe which may be blocked by a user to allow the fluid to traverse the length of the probe to exit the outlet.

In yet another embodiment of the first aspect, the channel may receive a tube which extends along a length of the channel and inside which the fluid travels.

In another embodiment of the first aspect, the heating element may be insulated.

In yet another embodiment of the first aspect, the heating element may be controlled by a feedback controller to maintain the heating element at a desired temperature.

In still another embodiment of the first aspect, the device may further comprise a thermocouple to measure the temperature of the fluid and provide the measured temperature to the feedback controller.

In another embodiment of the first aspect, the thermal emitter may be set to a temperature above the desired temperature for the exiting fluid to account for loss of heat before exiting the outlet.

In one embodiment of the first aspect, the exiting fluid may comprise a temperature in the range of 20-30° C. to desiccate at least one of the two or more tissues and/or surrounding area. The fluid exiting the outlet may comprise about 20, 21, 22, 23, 24, 25, 26, 27, 28, 29 or 30° C.

The desiccating fluid may be unheated or at least substantially unheated by the disruptive emitter.

In another embodiment of the first aspect, the exiting fluid may comprise dry air.

In one embodiment of the first aspect, the desiccating fluid does not cause a thermal effect on the two or more tissues.

The device of the first aspect may further comprise one or more of a pump, pressure regulator or flow meter.

The pump may provide a sterile, temperature-regulated fluid flow.

The device of the first aspect may further comprise a laser light source connected to the laser fibre.

In a second aspect, there is provided a device for treating a detached retina comprising:
a fluid pump to provide a sterile, temperature-regulated desiccating fluid flow; and a probe comprising an outlet for the sterile, temperature-regulated desiccating fluid flow so that the sterile, temperature-regulated desiccating fluid exiting the outlet may be directed to at least one of the two or more tissues and/or to a gap between the two or more tissues to dehydrate at least one of the two or more tissues and/or the gap.

In a preferred embodiment of the second aspect, the device is a device for treating or when used to treat a detached retina, the probe is an intraocular probe and the fluid is a gas.

According to either the first or second embodiment, wherein a detached retina is treated, the exiting fluid may be targeted to a retinal tear margin and at least a part of the retina bordering the retinal tear.

According to either the first or second embodiment, the exiting fluid may dehydrate the subretinal space exposed by the retinal tear.

According to either the first or second embodiment, at least a part of the retina bordering the retinal tear may be comprised in a targeted zone for dehydration.

The at least a part of the retina may be targeted to indirectly dehydrate the subretinal space over a broader retinal border.

The two or more tissues may comprise skin and/or a mucus membrane.

According to the second embodiment, the temperature of the desiccating fluid may comprise a temperature in the range of 20-30° C. The temperature of the desiccating fluid may comprise 20, 21, 22, 23, 24, 25, 26, 27, 28, 29 or 30° C.

In a preferred embodiment of the second aspect, the desiccating fluid does not cause a thermal effect on the two or more tissues.

The device of the second aspect may further comprise a disruptive emitter which emits a force to be directed at the two or more tissues sufficient to fuse the two or more tissues.

In one embodiment of the second aspect, the disruptive emitter comprises a fusion-causing emitter.

In another embodiment of the second aspect, the disruptive emitter comprises a thermal emitter or a light emitter. The thermal emitter may comprise a heat emitter or a cold emitter. The light emitter may comprise a laser fibre and a laser fibre tip.

The device of the second aspect may further comprise a fluid pump to provide a sterile, temperature-regulated thermal fluid flow which exits from an outlet in the probe to provide a sterile, temperature-regulated thermal fluid to be directed to at least one of the two or more tissues and/or a gap between the two or more tissues to thermally fuse the two or more tissues.

According to the second aspect, the thermal fluid may comprise a temperature in the range of 55-100° C.; 55-80° C.; 60-75° C.; or 62-70° C. The thermal fluid may comprise a temperature of 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100° C.

The device of the second aspect may further comprise a temperature regulator to regulate the temperature of the desiccating fluid and/or the thermal fluid.

The temperature regulator may comprise a heater and/or cooler.

The temperature regulator may be comprised on the pump or the probe.

The device of the second aspect may further comprise a pressure regulator to regulate the flow rate of the desiccating fluid and/or the thermal fluid.

The pressure regulator of the second aspect may be comprised on the pump or the probe. Preferably, the regulator is comprised on the probe to allow an operator to shut off flow when not required.

The desiccating fluid and/or the thermal fluid may comprise a gas or liquid. In a preferred embodiment, the desiccating fluid and/or the thermal fluid comprises a gas.

The gas may comprise air.

The device of the second aspect may also comprise a desiccating fluid source and/or thermal fluid source.

The desiccating fluid source and the thermal fluid source may comprise the same fluid source. The fluid source may comprise a source of compressed air such as, one or more tanks.

In one embodiment of the second aspect, the thermal emitter comprises a heating element disposed inside a channel, the channel and the outlet in fluid communication, the heating element for heating the fluid so that fluid exiting the outlet comprises a temperature sufficient to fuse the two or more tissues.

According to the second embodiment, the heating element may be located at a proximal end of the probe to minimise any offset in temperature before fluid exits the outlet.

According to the second embodiment, the heating element may comprise a coil. The coil may be comprised of a nichrome wire.

According to the second embodiment, thermal emitter may heat the fluid to a temperature so that the exiting fluid may comprise a temperature in the range of 55-100° C.; 55-80° C.; 60-75° C.; or 62-70° C. to thermally fuse the two or more tissues. The thermal emitter may heat the fluid to a temperature of 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100° C.

In another embodiment of the second aspect, the heating element comprises a blind tip of a laser fibre.

In still another embodiment of the second aspect, the light emitter comprises a laser fibre disposed on the hand held probe which emits laser light sufficient to fuse the two or more tissues.

According to one embodiment of the second aspect, the device may further comprise a detachable tip which may be joined in fluid communication with the hand held probe to allow passage of the fluid from the hand held probe to the detachable tip so that fluid exits out of the detachable tip.

In another embodiment of the second aspect, the hand held probe may comprise an orifice along a length of the probe which may be blocked by a user to allow the fluid to traverse the length of the probe to exit the outlet.

In yet another embodiment of the second aspect, the channel may receive a tube which extends along a length of the channel and inside which the fluid travels.

In another embodiment of the second aspect, the heating element may be insulated.

In yet another embodiment of the second aspect, the heating element may be controlled by a feedback controller to maintain the heating element at a desired temperature.

In still another embodiment of the second aspect, the device may further comprise a thermocouple to measure the temperature of the fluid and provide the measured temperature to the feedback controller.

In another embodiment of the second aspect, the thermal emitter may be set to a temperature above the desired temperature for the exiting fluid to account for loss of heat before exiting the outlet.

The device of the second aspect may further comprise a laser light source connected to the laser fibre.

The device of the first or second aspect may further comprise an outlet for a therapeutic composition to be applied to one or more interface between the two or more tissues.

The therapeutic composition may comprise a proteinaceous fluid.

The proteinaceous fluid may comprise albumin.

The albumin may comprise blood albumin, egg albumin or synthetic albumin.

The therapeutic fluid may comprise collagen fibre to provide some temporary structure and a scaffold for repair over time to increase wound strength.

The therapeutic composition may comprise a gel.

Preferably, the therapeutic composition is added after the dessicating fluid and before the thermal fluid.

The device of the first or second aspect may further comprise one or more filters through which the desiccating fluid and/or the thermal fluid flows to provide sterility. The one or more filters may comprise a microbiological filter.

The one or more filters may comprise a Millepore filter.

The intraocular probe of the first or second aspect may comprise a curved tip to minimise the risk of touching the back of the optical lens.

The curved tip may comprise a shape memory.

In the preferred embodiment in which the device of the first or second embodiment is a device for repairing a detached retinal, the retina and the retinal pigmented epithelium are thermally fused.

According to the second embodiment, the outlet for the desiccating fluid and the outlet for the thermal fluid may be the same outlet.

The outlet may be comprised on a thin tip.

The device of the first or second embodiment may further comprise a fibre-optic cable connected to a video viewing device.

The fluid pump which provides the desiccating fluid flow and the fluid pump which provides the thermal fluid flow may be the same fluid pump.

According to the device of the first or second aspect, tissue injury may be minimized, or at least substantially reduced.

According to the device of the first or second aspect, an inflammatory response is substantially reduced or eliminated.

In a third aspect, there is provided a method for fusing two or more tissues using the device of the first aspect or the device of the second aspect.

In a fourth aspect, there is provided a method for fusing two or more tissues, the method comprising: providing a sterile, temperature-regulated desiccating fluid flow which exits out of a probe so that the sterile, temperature-regulated fluid flows to at least one of the two or more tissues and/or to a gap between the two or more tissues; and directing a disruptive emission to at least one of the two or more tissues and/or the gap sufficient to fuse the two or more tissues.

In one embodiment of the fourth aspect, the disruptive emission comprises a fusion-causing emission.

In another embodiment of the fourth aspect, the disruptive emission comprises a thermal emission or a light emission. The thermal emission may comprise a heat emission or a cold emission. The light emission may be from a laser fibre and a laser fibre tip.

In a preferred embodiment, the method of the fourth aspect is a method for treating a detached retina, the probe is an intraocular probe and the fluid is a gas.

According to the fourth aspect, in the embodiment wherein a detached retina is treated, the exiting fluid may be targeted to a retinal tear margin and at least a part of the retina bordering the retinal tear.

According to the fourth aspect, the exiting fluid may dehydrate the subretinal space exposed by the retinal tear.

According to the fourth aspect, the at least a part of the retina bordering the retinal tear may be a targeted zone of the retina bordering the retinal tear.

According to the fourth aspect, the at least a part of the retina may be targeted to indirectly dehydrate the subretinal space over a broader retinal border.

According to the fourth aspect the two or more tissues may comprise skin and/or a mucous membrane.

According to the fourth aspect the temperature of the desiccating fluid may be regulated between 20-30° C. The temperature of the desiccating fluid may comprise 20, 21, 22, 23, 24, 25, 26, 27, 28, 29 or 30° C.

In a preferred embodiment, the desiccating fluid does not cause a thermal effect on the two or more tissues.

According to the fourth aspect, the disruptive emission may comprise a sterile, temperature-regulated thermal fluid flow which exits as a sterile, temperature-regulated thermal fluid out the probe to thermally fuse the two or more tissues.

In the preferred embodiment in which the method of the fourth aspect is a method for treating a detached retina, the retina and the retinal pigmented epithelium are thermally fused.

The thermal fluid may comprise a temperature of between 55-100° C.; 55-80° C.; 60-75° C.; or 62-70° C. The thermal fluid may comprise a temperature of 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100° C.

According to the fourth aspect, wherein the method is a method for treating a detached retina, the method may further comprise exiting the desiccating and/or thermal fluid out of a curved tip in the intraocular probe to minimise the risk of touching the back of the lens.

The method of the fourth aspect may further comprise heating and/or cooling the desiccating fluid and/or the thermal fluid to thereby regulate the temperature.

The method of the fourth aspect may further comprise regulating the pressure of the desiccating fluid and/or the thermal fluid.

In yet another embodiment of the fourth aspect, the disruptive emission may be heated by a heating element disposed inside a channel comprised in a hand held probe so that exiting fluid comprises a temperature sufficient to fuse the two or more tissues.

According to the fourth aspect, the heating element may be located at a proximal end of the probe to minimise any offset in temperature before fluid exits the outlet.

According to the fourth aspect, the heating element may comprise a coil. The coil may be comprised of a nichrome wire.

According to the fourth aspect, the heating element may heat the fluid to a temperature so that the exiting fluid may comprise between 55-100° C.; 55-80° C.; 60-75° C.; or 62-70° C.

The thermal emitter may heat the fluid to a temperature of 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100° C.

In yet another embodiment of the fourth aspect, the method may further comprise using feedback control to maintain the heating element at a desired temperature.

In still another embodiment of the fourth aspect, the method may further comprise obtaining a temperature of the heating element or of the thermal emission.

In another embodiment of the fourth aspect, the method may further comprise setting the thermal emitter to a temperature above the desired temperature for the exiting fluid to account for loss of heat before exiting the outlet.

According to the fourth aspect, the desiccating fluid and/or the thermal fluid may comprise a gas or liquid. In a preferred embodiment, the desiccating fluid and/or the thermal fluid comprise a gas.

According to the fourth aspect, the gas may comprise air.

According to the fourth aspect, the method may further comprise providing a fluid source.

According to the fourth aspect, the fluid source may comprise a compressed air source such as, one or more tank.

The method of the fourth aspect may further comprise a step of applying an indicator to determine sufficient desiccation. The indicator may comprise a dye. The dye may comprise fluorescein.

The method of the fourth aspect may further comprise a step of applying a therapeutic composition to one or more interface between the two or more tissues.

The therapeutic composition may comprise a proteinaceous fluid such as, an albumin, like blood albumin, egg albumin or synthetic albumin. The therapeutic fluid may comprise collagen fibre to provide some temporary structure and a scaffold for repair over time to increase wound strength.

In one embodiment, the therapeutic composition comprises a gel.

Preferably, the therapeutic composition is added after the dessicating fluid and before the thermal fluid.

The method of the fourth aspect may further comprise filtering the desiccating fluid and/or the thermal fluid through one or more filters to provide sterility. The one or more filters used to perform the filtering may comprise a microbiological filter.

According to the fourth aspect, the one or more filters may comprise one or more Millepore filter.

The method of the fourth aspect may further comprise heating the two or more tissues with a thermal probe.

According to the fourth aspect wherein the method is a method of treating a detached retina, the two or more tissues heated with the thermal probe may be the retina and/or retinal pigmented epithelium.

The thermal probe may comprise a laser fibre-optic cable with a blind tip.

In one embodiment, the subject is a human.

According to the method of the fourth aspect, tissue injury may be minimized, or at least substantially reduced.

According to the method of the fourth aspect, an inflammatory response is substantially reduced or eliminated.

The method of the third or fourth aspect may further comprise the step of adding perfluorocarbon liquid or performing a fluid gas exchange to drain or partially drain subretinal fluid.

The method of the fourth aspect may further comprise viewing the amount of meniscus fluid left at the edge of the retina tear edge through a fiber optic cable in the probe.

According to any one of the above aspects or embodiments, the treatment of the detached retina may comprise direct fusion of the retina and retinal pigmented epithelium.

According to any one of the above aspects, the fusion of the retina and retinal pigmented epithelium may be instant.

The invention also provides a device and a method substantially as herein described with or without reference to the examples and figures.

As used herein, except where the context requires otherwise, the term "comprise" and variations of the term, such as "comprising", "comprises" and "comprised", are not intended to exclude further additives, components, integers or steps.

Although the invention is described with reference to repair of retinal detachment it is understood that the invention may be applied to fusion of two or more tissues generally. Suitable tissues include skin and/or a mucous membrane.

As used herein, "tissue detachment" includes tissue that is detached or otherwise separated such as, skin or mucous membranes that have split, torn or have been cut into.

In one embodiment, the present invention is, at least in part, predicated on the inventor's surprising discovery that retinal detachment may be repaired using direct fusion. The inventor's method and device has the significant advantage of providing an instant fusion as opposed to conventional methods which rely on the protracted fusion resulting as a byproduct of the induced inflammatory response. Another advantage of this embodiment of the present invention is minimizing, or at least substantially reducing, tissue injury and substantially reducing or eliminating any inflammatory response. The skilled person will appreciate that due to the instant and direct nature of the tissue bonding by the present invention yet another advantage is that redetachment may be eliminated or the rate thereof substantially reduced.

Retinal reattachment requires closing the retinal tear. Traditionally, this has been achieved by wound healing. Through diligent study, the inventor has developed a device and method for repair of retinal detachment which has achieved fusion of the retina to the RPE with an instant seal. In one embodiment, the present invention achieves this by effectively spot-welding the tear boundary to the underlying tissue. This novel technique is described herein and is expected to significantly increase surgical success rates and shorten surgical times.

The retinal pigmented epithelium (RPE) is the tissue layer between the light detecting neurosensory retina and the underlying vascular bed (the choroid). The RPE plays a critical role in vision: it both performs the chemical conversion of the light sensitive chemicals (rhodopsin and derivatives) from light exposed/"spent" to light sensitive, and, pumps water from the subretinal space to the choroid to keep the retina attached. When the retina is detached from the RPE, a subretinal space (SRS) is created between the retina and the RPE which is filled with water and, over time, macromolecules from the blood (a transudate or filtrate) alter the SRS chemistry.

As used herein "disruptive" is used to refer to causing a disruption from the normal state of the tissue. The disruption may comprise an injury such as a thermal injury or ablation or other change in state. The disruption may be sufficient for the tissue to fuse to another tissue. The fusion may be a direct fusion of two tissues or may be the result of new tissue produced as a result of the healing of the injury induced by the disruption.

FIG. 1. shows one embodiment of a device 100 for treating a detached retina according to the invention. Device 100 comprises a fluid pump 110 to provide a flow of sterile, temperature-regulated desiccating fluid 112 through device 100.

Device 100 also comprises an intraocular probe 120 comprising a probe body 121 on which an outlet 122 for the sterile, temperature-regulated desiccating fluid flow is disposed so that the sterile, temperature-regulated desiccating fluid 112 exiting outlet 122 may be targeted to the retina to dehydrate the retina and/or retinal pigmented epithelium.

In device 100, the outlet 122 is comprised on a thin tip 124 designed for intraocular surgery.

Tip 124 is comprised of any suitable metal or polymer. Based on the teachings herein, a skilled person is readily able to select a suitable material for tip 124.

Tip 124 comprises a 20-27 gauge. The gauge may be 20, 21, 22, 23, 24, 25, 26 or 27. As shown in the FIG. 1, tip 124 comprises two stages. Namely, a thicker outer stage 124a and a thinner inner stage 124b. The inner stage 124b is flexible and can be extruded as far as necessary and closer to the retina. In one embodiment, the outer stage 124a is comprised of a metal and the inner stage 124b is comprised of a polymeric material. From the teachings herein, a skilled person is readily able to select other suitable materials for the outer stage 124a and the inner stage 124b.

In other embodiments, tip 124 comprises a single stage, which may be more difficult to control getting into the eye than the two-stage embodiment.

Based on the teaching herein, a skilled person is readily able to select a suitable tip for tip 124, such as conventional tips available for removal of subretinal fluid.

The temperature of the desiccating fluid 112 is selected to desiccate or dry out the retina and/or the RPE without causing any thermal damage. Suitable temperature ranges for the desiccating fluid may comprise a temperature in the range of 20-30° C. The temperature of the desiccating fluid may comprise 20, 21, 22, 23, 24, 25, 26, 27, 28, 29 or 30° C.

The desiccating fluid 112 may be directed at or over the retinal defect or tear margin to desiccate the retina around the defect or tear. The desiccation may result in drying of the exposed RPE and the meniscus at the junction of the retina and RPE so that the meniscus disappears. The temperature of fluid 112 may be increased such that it comprises a sterile, temperature-regulated thermal fluid flow which exits from outlet 122 to provide a sterile, temperature-regulated thermal fluid 112 to target the retina and/or the retinal pigmented epithelium for thermal fusion.

The temperature of the thermal fluid 112 is selected to induce direct fusion of the retina and the retinal pigmented epithelium without causing further deleterious effects. The temperature of the thermal fluid 112 may comprise a temperature in the range of 55-100° C.; 55-80; 60-75° C.; or 62-70° C. The thermal fluid may comprise a temperature of 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100° C.

While not wanting to be bound by any one theory, the inventor hypothesises that a temperature in the range of 55-80° C. should be sufficient to result in thermal fusion. The inventor also extends this hypothesis by noting that some inflammation may be better to anchor the RPE to the underlying choroid more effectively. For this reason, a higher temperature, up to 100° C., may be useful.

Advantageously, application of the desiccating fluid 112 to the edge of the retinal tear will remove the meniscus of subretinal fluid at the edge of the tear. Further, application to the area surrounding the retina indirectly dehydrates the subretinal space and allows fusion.

Device 100 may further comprise a temperature regulator 126 to regulate the temperature of the desiccating fluid 112 and/or the thermal fluid 112 through the tip 122. In the embodiment shown the temperature regulator 126 is comprised on probe 120. In other embodiments temperature regulator is not on probe 120 and may comprise a separate component or part of an assembly comprising one or more of pump 110, pressure regulator 114 or filter 116.

The temperature regulator 126 is comprised on pump 110. The temperature regulator 126 may comprise a heater (not shown) and/or cooler (not shown).

Device 100 may further comprise a pressure regulator 114 to regulate the flow rate of the desiccating fluid and/or the thermal fluid. Based on the teaching herein, a skilled person is readily able to select a suitable flow rate for fluid 112. In the embodiment shown, the pressure regulator 114 is comprised on pump 110. This may be preferable to many operators because it allows flow to be shut off when not required. In other embodiments, pressure regulator 114 is comprised on probe 120.

In one embodiment, pressure regulator 114 may comprise a passive opening (not shown) that allows air to escape (outside the eye) prior to entering the high resistance narrow tube that comprises outlet 122 which actually goes into the eye. In another embodiment, pressure regulator 114 may comprise a modified valve such as a clip (not shown) with a hole (not shown) that can be slid over a hole in the shaft (not shown) so that it is either fully open or partially open (similar to a valve on a vacuum cleaner shaft).

In the embodiment shown, desiccating fluid 112 and thermal fluid 112 comprises air. Based on the teachings herein, a skilled person is readily able to select other suitable gases or liquids to comprise the desiccating fluid 112 and the thermal fluid 112. In preferred embodiments, the desiccating fluid and the thermal fluid comprises a gas.

The device may also comprise a desiccating fluid source and/or thermal fluid source (not shown). Device 100 utilises the same compressed air tank (not shown) for provision of both desiccating fluid 112 and thermal fluid 112. In other embodiments, the device comprises a desiccating fluid source that is separate from the thermal fluid source.

Fluid 112 flows through tubing 111 from pump 110, through filter 116 and pressure regulator 114 into probe 120, through tip 124 and out of outlet 122.

Device 100 may further comprise an outlet for a therapeutic composition to be applied to one or more interfaces between the two or more tissues. The outlet for the therapeutic composition may be outlet 122 or may be on a second probe (not shown).

The therapeutic composition may comprise a proteinaceous fluid. The proteinaceous fluid may comprise albumin. The albumin may be blood albumin, egg albumin or synthetic albumin.

The therapeutic fluid may comprise collagen fibre to provide some temporary structure and a scaffold for repair over time to increase wound strength.

The therapeutic composition may comprise a gel.

Preferably, the therapeutic composition is added after the dessicating fluid and before the thermal fluid.

Device 100 further comprises a 22 µ Millipore filter 116 through which the desiccating fluid 112 and/or the thermal fluid 112 flow to provide sterility. Based on the teaching herein a person of skill in the art is readily able to select other suitable filters.

In other embodiments, device 100 comprises a plurality of filters 116.

In device 100 probe tip 124 is curved to minimise the risk of touching the back of the optical lens which would cause a cataract. Curved tip 124 adopts the curved shaped by comprising a shape memory such that as it comes out of a sleeve (not shown) the curved shape is adopted.

In one embodiment, the exiting fluid 112 is targeted to a retinal tear margin and at least a part of the retina bordering the retinal tear. This is so that the exiting fluid 112 can be used to dehydrate the subretinal space exposed by the retinal tear. The part of the retina bordering the retinal tear, the RPE adjacent the tear and/or the gap in between the retina and the RPE may be part of a targeted zone. The targeted zone comprises a region targeted to indirectly dehydrate the subretinal space over a broader retinal border.

Figure 2:
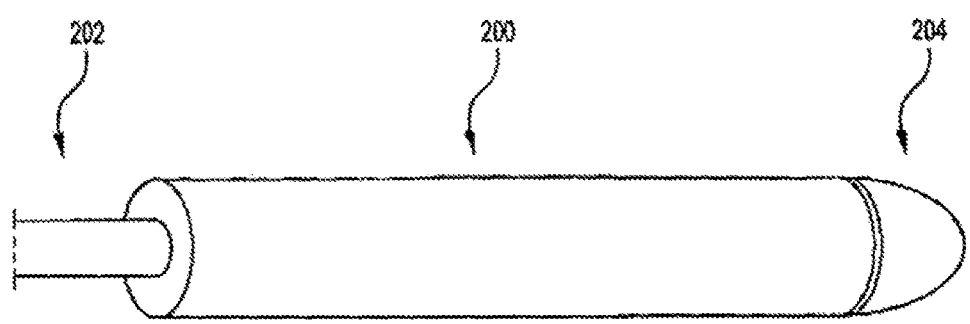
FIG. 2: shows one embodiment of a thermal probe according to the invention.

Device 100 may also comprise a thermal probe for heating the retina and/or the retinal pigmented epithelium. FIG. 2 shows one embodiment of a thermal probe 200. The thermal probe 200 comprises a laser fibre-optic cable 202 which ends in a blind tip 204 to provide a heat source.

Device 100 may further comprise a fibre-optic cable (not shown) connected to a video viewing device (not shown). The fibre-optic cable may be comprised in the intraocular probe 120 and be connected to a video viewing device, so that the amount of meniscus fluid left at the edge of the retinal tear edge can be seen at high magnification, rather than down the operating microscope. This will give a detailed view of the degree of retinal dehydration.

Figure 7:
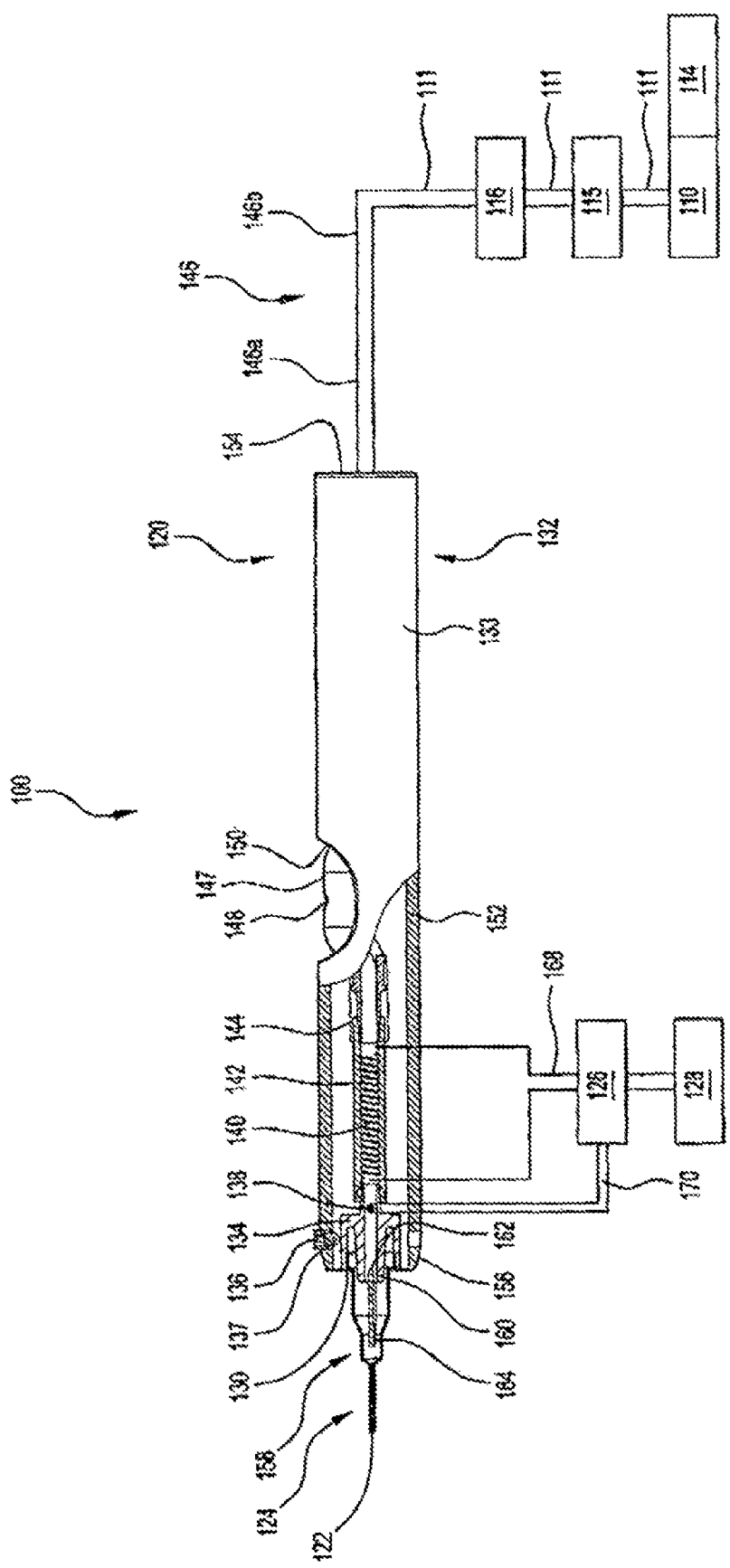
FIG. 7: a schematic diagram showing another embodiment of a device according to the invention.
Figure 8:
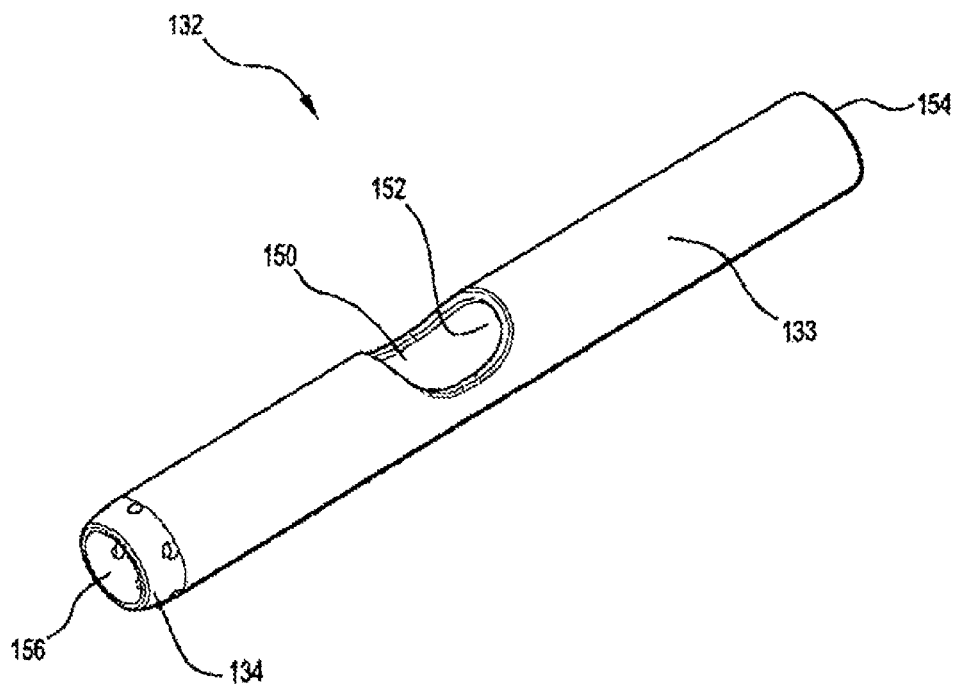
FIG. 8: a schematic diagram showing one embodiment of a handpiece according to the invention.

A second embodiment of a device 100 according to the invention is shown in FIG. 7. Device 100 of the second embodiment comprises the intraocular probe 120, pump 110, filter 116, pressure regulator 114 and outlet 122 as well as the additional features discussed below.

FIG. 7 shows intraocular probe 120 to be comprised of a handpiece 132 and a detachable thin tip 124 which are joined by connecting the tip connector 130 on tip body 158 and handpiece connector 134 on handpiece 132. In the embodiment shown, connectors 130 and 134 are male and female luer locks, respectively. A skilled person is readily able to select other suitable connectors.

To allow mating with differently sized thin tips 124, handpiece 132 comprises an adaptor 136 which is received in housing 137. When adaptor 136 is removed, a larger thin tip 124, or larger connector 130 may be connected to connector 134.

In the second embodiment, thin tip 124 is disposable and comprises a tip body 158 comprising a needle comprising a needle channel 164 that ends at a proximal end in outlet 122. The needle channel 164 also comprises at its distal end a needle opening 162 which connects to handpiece tubing 144 at a junction between needle opening to tubing 162 and tubing opening to needle 160.

Heating element 140 is enclosed by heating element insulation 142 all of which is positioned inside handpiece tubing 144.

To allow simple application of fluid 112, handpiece 132 comprises an opening 150 which houses handpiece tubing presentation 147 on which an orifice 148 in tubing 144 is disposed. A user can occlude orifice 148 to direct fluid 112 to exit outlet 122.

Handpiece tubing 144 traverses the length of channel 152 and joins to external tubing 111 at connection 146. Connection 146 comprises connection on handpiece tubing 146a and connection 146b on external tubing 111 which mate to provide a fluid connection.

Handpiece 132 comprises an elongate body 133 comprising a channel 152 running along its length and which opens to a fluid receiving opening 154 at a distal end and a fluid exit opening 174 at proximal or tip receiving end 156. Elongate body 133 is adapted to be held in a user's hand and to allow aiming of the tip 124 at the target area.

In the second embodiment, a heating element 140 is disposed inside channel 152 for heating fluid 112. Advantageously, heating element 140 is located at the proximal end of handpiece 132 to minimise any offset in temperature before fluid 112 exits outlet 122. Testing has shown the proximal location of heating element 140 is more effective in delivering heat than the embodiment of FIG. 1 which loses heat along the length of tubing 111.

To account for the offset in temperature that will occur between fluid 112 being heated at the location of the element 140 and the temperature exiting outlet 122, element 140 may be heated to a temperature above the desired temperature at outlet 122. The offset, that is, the amount the element temperature is above the desired temperature, may be in the range of 5-50° C. or in the range of 5-25° C. The offset may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50° C.

To maintain an accurate temperature, element 140 is connected to heater 128 and temperature regulator 126. Temperature regulator 128 is also connected to thermocouple 138 which is located downstream of element 140. Thermocouple provides a reading of fluid temperature to the temperature regulator which adjusts the output of heater 128 so that the temperature of element 140 is varied accordingly.

In the embodiment shown in FIG. 7, regulator 128 comprises a proportional-integral-derivative controller which can vary the current which heater 128 provides to element 140 to thereby equalise the measured temperature at thermocouple 138 versus the temperature setting for element 142.

FIG. 7 shows the heating element to comprise a coil comprised of a nichrome wire. The nichrome wire is wound to a desired resistance. Heat is produced by passing current through the wire.

In the embodiment shown in FIG. 7, handpiece 132 is comprised of acetal. In other embodiments, the handpiece is comprised of a medical grade, biocompatible material that can be sterilized such as, a polycarbonate.

Handpiece 132 comprises a length of 13 cm and thin tip 124 comprises a 27 gauge dispensing blunt tip needle from Zephyrtronics. Based on the teaching herein, a skilled person is readily able to select other suitable lengths and tips 124.

Figure 9:
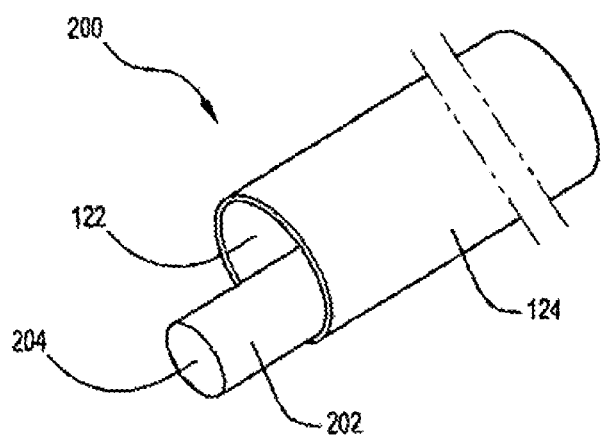
FIG. 9: a schematic diagram showing the tip of an embodiment of a device comprising a laser fibre according to the invention.
Figure 10:
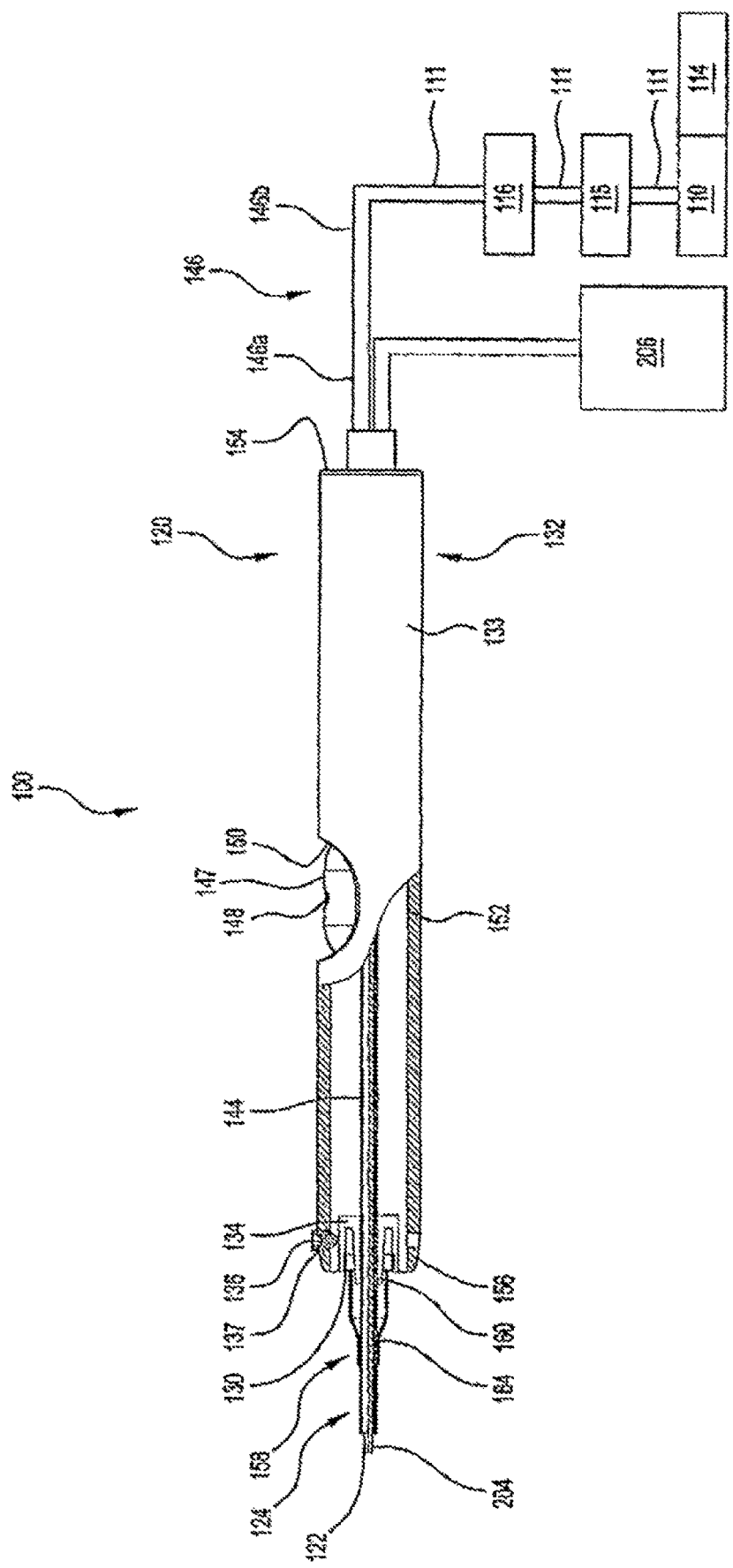
FIG. 10: a schematic diagram showing a side view of the embodiment shown in FIG. 9.

FIGS. 9 and 10 show another embodiment of device 100 according to the invention. FIG. 9 shows a close up perspective view of tip 124 showing a fibreoptic cable 202 comprising a blind tip 204 which provides the disruptive energy in the form of heat. FIG. 10 shows the entire device 100 according to this embodiment showing that heater 128, temperature regulator 126, temperature sensor 138, heating element 140, insulation 142 and lines 168 and 170 are replaced with fibre optic cable 202 which is connected to a laser source 206.

Laser handpiece 100 is used similarly to conventional laser eye surgery but at lower energy levels so as to create a disruption for fusion rather than in the form of a thermal injury or burn which forms scar tissue to seal the retina to the RPE.

The inventor has also provided a method for treating a detached retina using the device 100.

According to a method of the invention, a sterile, temperature-regulated desiccating fluid flow is provided which exits out of the intraocular probe 120 so that the sterile, temperature-regulated fluid 112 flows to the retinal surface to dehydrate the retina, the meniscus at the tear margin and the subretinal space and/or the adjacent RPE to thereby prepare the retina and RPE/choroid for fusion of the detached retina.

The method may further comprise a step of providing a sterile, temperature-regulated thermal fluid flow which exits as a sterile, temperature-regulated thermal fluid 112 out of the intraocular probe 120 to thermally fuse the retina and/or the RPE.

The method may further comprise irradiation of the dehydrated retina and subretinal space with laser light as a disruptive force elevating the tissue temperature in the range of 70-100° C.

The method may further comprise viewing the amount of meniscus fluid left at the edge of the retina tear edge through a fiber optic cable in the probe.

The method may further comprise staining the fluid meniscus with fluorescein or another agent to reveal a persistent fluid meniscus. The fluorescein will fluoresce green when fluid is present and may be used to indicate sufficient dehydration. The fluorescein may be delivered with a dripper or mixed in Healon.

The method may further comprise the step of adding perfluorocarbon liquid or performing a fluid gas exchange to drain or partially drain subretinal fluid. This step may remove the SRF under the macula that specialised retinal region that gives central vision. This step is an optional step because it is not essential to reattach the retinal tear margin in most cases. Based on the teaching herein, a skilled person will be readily able to select instances in which this optional step is required or may be of benefit.

EXAMPLES

The following non-limiting examples illustrate the device and methods of the invention. These examples should not be construed as limiting: the examples are included for the purposes of illustration only. The device and method discussed in the Examples will be understood to represent an exemplification of the invention.

Example 1

The closure of retinal tears has traditionally been achieved by inducing inflammation of both the RPE and retina. While not wanting to be bound by any one theory, the inventor's hypothesis that removing the subretinal fluid should allow direct thermal fusion of both (hydrophobic) lipoprotein layers. Here, the inventor reports the histological findings in an animal model of rhegmatogenous retinal detachment.

Material and Methods:

Localised retinal detachment (RD) was created in pigmented rabbit eyes and a traditional fluid gas exchange performed. Dehydration of the subretinal space was achieved with a directed air stream prior to laser coagulation. The vitreous cavity was returned to BSS and the eyes enucleated and fixed.

The 9 Dutch-belted pigmented rabbits underwent vitrectomy with lensectomy, creation of localised retinal detachment by subretinal BSS injection, enlargement of the hole with the vitrector, fluid-gas exchange and then dehydration of the hole margin with an airstream. Laser (810 nm) was then applied to achieve a mild whitening of the margin and the BSS irrigation resumed. Eyes were then enucleated and the treated retina examined histologically.

Laser Thermofusion Study Technique:

Laser thermofusion of retina and pigment epithelium: the experiments were approved by the Animal Research and Ethics Committee (project 09/178AR), Royal Victorian Eye and Ear Hospital (RVEEH), Melbourne, Australia.

Adult pigmented rabbits were sedated and underwent vitrectomy and lensectomy (ALCON Accurus®) to create a large unicameral eye. It was necessary to remove the lens because it is so large in the rabbit eye that it would not allow retinal detachment to be peripheral enough to prevent fluid recruitment keeping the retinotomy moist.

The rabbits were anaesthetised using a standard protocol (Pre-med Acetylpromazine s/c 1 mg/kg Ketamine 35 mg/kg and Xylazine 5 mg/kg mixed together and given as an I/M injection with a 1/6 dose rate of the original used to augment the sedation if there were any signs of lightening. Topical amethocaine drops were applied followed by subconjunctival Xylocaine 2%.

The pupils were dilated with tropicamide 1.0% and phenylephrine 10%.

The rabbits were positioned on a warming pad under the operating microscope and a lid speculum inserted. They underwent routine vitreoretinal surgery utilizing the Landers widefield vitrectomy system with PWL lens and 23 gauge (23 g) cannulae (ALCON Accurus system) were inserted. A Fragmatome lensectomy was performed to achieve adequate vitreous volume for the surgery and minimize fluid accumulation during the laser treatment.

A retinal detachment was created by injecting balanced salt solution (BSS) under the retina into the subretinal space through a soft-tipped 23 g cannula to create a localized bleb of retinal detachment.

The retinal defect was enlarged with the vitrector to mimic the type of retinal tear found during retinal detachment surgery. A standard fluid gas exchange filled the vitreous cavity with air and residual fluid was repeatedly aspirated using 23 g soft-tip cannula through the retinal defect/tear as in traditional vitreoretinal surgery.

Dehydration of the retinal tear margin and underlying subretinal space was then achieved with a separate airstream directed from a 23 g fluid gas soft tip needle. The airflow was from an independent aquarium ("fish tank") air pump through a Millepore filter, to ensure bacteriological sterility, and connected to a backflush flute (ALCON 23 Ga Advanced Backflush Soft Tip) so that the vitreous cavity air pressurization infusion from the Accurus console was not affected.

The air stream was directed over the retinal defect/tear margin to desiccate the retina around the defect/tear. The airstream was controlled by pressure on the vent hole on the handle. The treated retina gradually became darker and appeared thinner than the surrounding area. The "sheen" of fluid on the exposed pigment epithelium and the meniscus at the junction of the retina and RPE disappeared. The area subjected to the air stream drying looked relatively "lifeless" with a matte surface reflection.

Adequate dehydration was judged when the sheen from the fluid meniscus where the retinal margin joined the exposed RPE layer was lost, the adjacent retinal surface had a matt reflex and the treated retina appeared darker and thinner.

Laser treatment (810 nm) was applied as repeated long applications (2000 ms) around the defect/tear margin, which was intense enough to produce some opacification of the treated retina. Laser treatment was with a standard fibre-optic probe over the retinal margin.

The BSS infusion was then recommenced and the manipulation cannulae removed and the scleral wounds closed. Formaldehyde was infused into the eye via the remaining infusion port after sacrifice of the animal (Ketamine 35 mg/kg×Xylazine 5 mg/kg mixed together and given as an I/M injection-followed by barbiturate of 2 mg/kg I/V or I/P injection), that sclera wound closed and the entire globe immersed in formaldehyde. The eyes were embedded whole to prevent tissue distortion and disruption of the retinal/RPE orientation. Step sections were cut until the treated areas found and then thin sections cut through the entire treated area.

Results:

The dehydrated retinal margin demonstrated thermal changes and fusion of the retina and RPE/choroid but the non-dehydrated adjacent retina and RPE remained separated by persistent subretinal fluid despite similar thermal tissue changes.

Fusion of the retina and pigment epithelium was demonstrated histologically in the areas of desiccated subretinal space. The surrounding areas showed residual subretinal fluid, thermal changes in the retina and RPE/choroid but no fusion.

Figure 3:
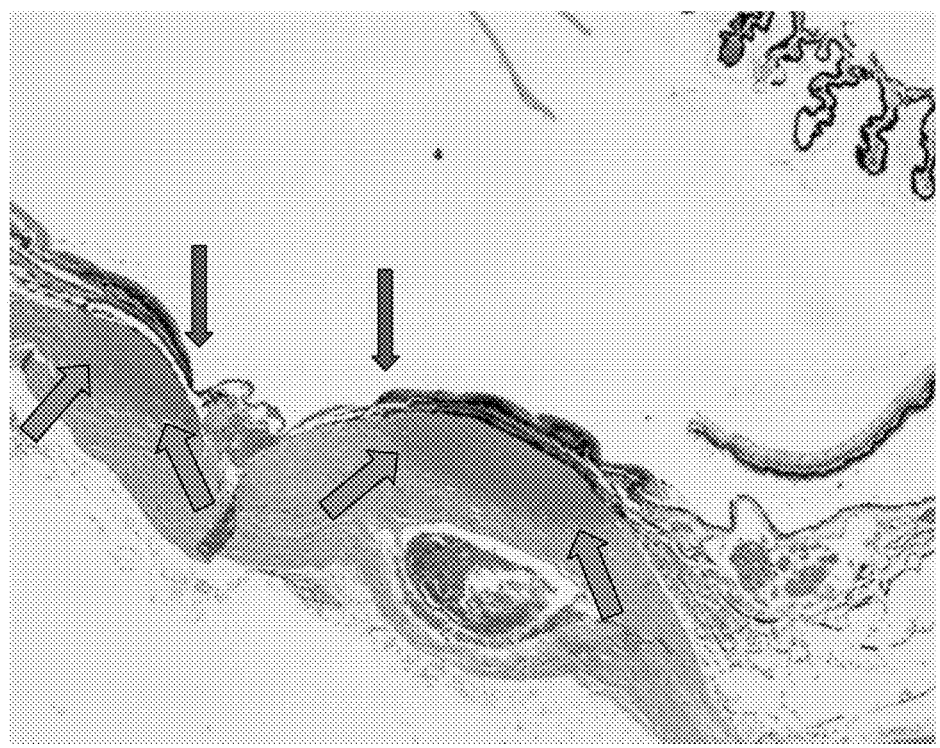
FIG. 3: Photomicrograph of rabbit eye treated then enucleated: Section through the retinotomy (bounded by blue (downward pointing) arrows) showing retinal and RPE/choroidal fusion in the dehydrated zone but persistent fluid at the perimeter of the iatrogenic detachment (upper left). Thermal changes in the retina RPE/choroid and underlying sclera outlined by yellow (upward pointing) arrows on both sides of the retinotomy margin (light photomicrograph (H6931 L20×4).

Light micrographs of the retina showed a thinned retina at the margin of the iatrogenic tear with extensive eosinophilic thermal change with apparent fusion of the retina, RPE and choroid (FIG. 3). Retinal and RPE/choroidal fusion is shown in the dehydrated zone but persistent fluid at the perimeter of the iatrogenic detachment is shown in the upper left.

Figure 4:
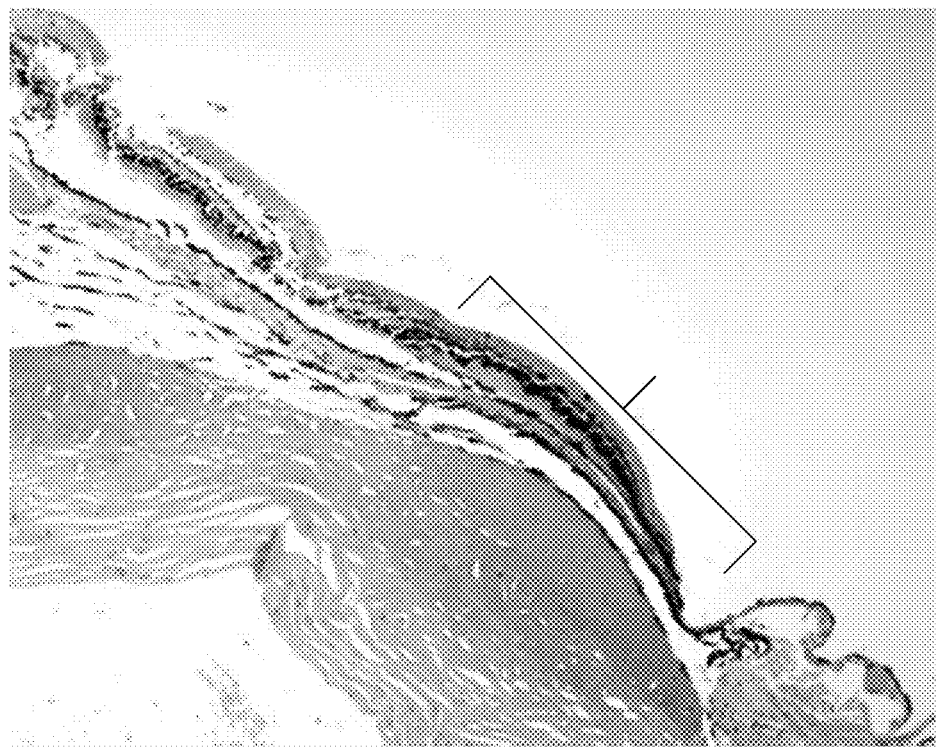
FIG. 4: higher magnification of treated retinotomy margin from FIG. 3., demonstrating the thinner (dehydrated) retina (bracket) with fusion of retina and RPE with elimination of the subretinal space in contrast to the non-dehydrated retina with thermal color change in retina and sclera but normal retinal layers (with some artifactual separation) and separation of the photoreceptor outer segments and RPE by the persistent subretinal fluid (SRF). (H6931 L20×10b).
Figure 5:
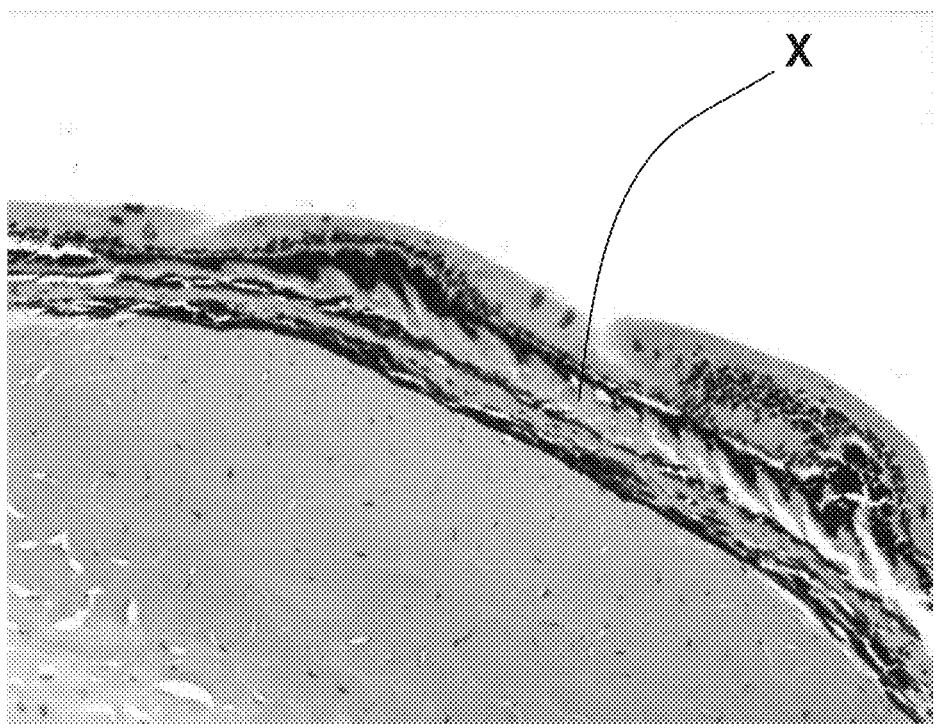
FIG. 5: high power photomicrograph demonstrating the outer segments fused to the RPE indicated by "X" (H6931 L20×20a).

Ten animals underwent the standard surgical protocol outlined above. They were found to have similar histological findings: the retina and RPE bounding the tear were fused as one mass (FIGS. 3-5). This was characterized by: reduced retinal thickness, strong eosinophilic staining of the retina and adjacent choroid, integration with the RPE (often artifactually separated from Bruch's membrane during preparation), occasional intraretinal vacuole formation (presumably intraretinal steam formation) and extensive thermal reaction in the underlying sclera.

In contrast, the remainder of the surgically detached retina surrounding the dehydrated tear margin showed thermal changes in the retina and underlying choroid and sclera without fusion—there was persistent SRF separating the retina and the RPE. Both (2) "control eyes", where standard detachment repair surgery was performed but without the specific retinal drying, demonstrated persistent separation of the photoreceptor outer segments and the RPE in the detached areas despite laser treatment of the tear margin (which was not exposed to the "air dryer" treatment).

Figure 6:
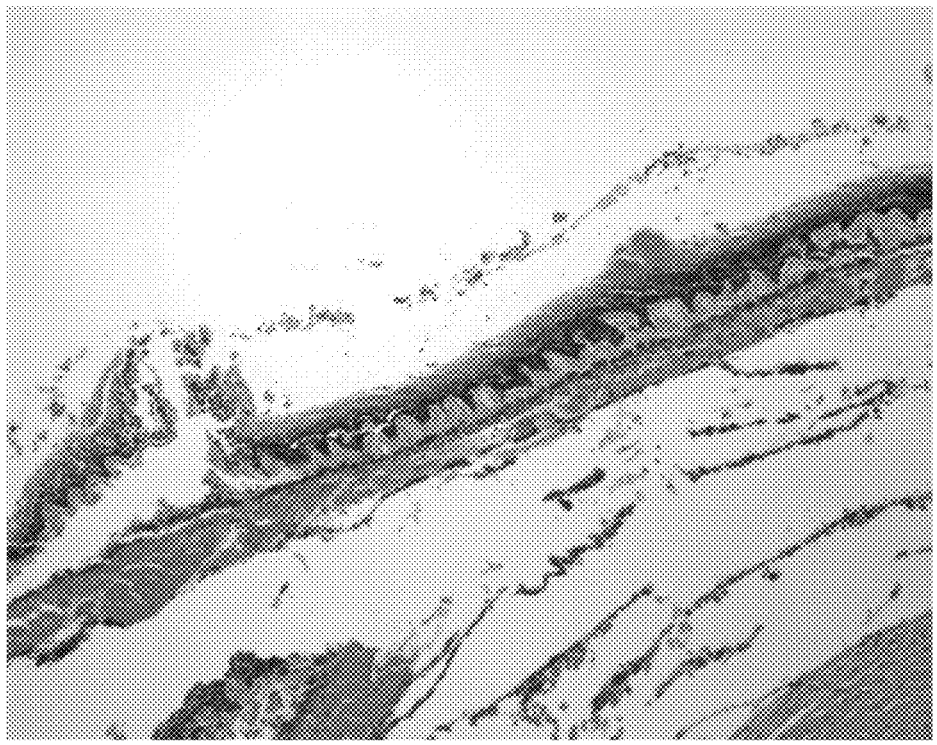
FIG. 6: Day 3 images show that 3 days following the surgery the retina and RPE remain fused without traditional "tamponade". There is a mild inflammatory reaction making the tissues hypercellular but the fusion is clearly preserved.

FIG. 6 is an image taken at Day 3 which shows that 3 days after the surgery the retina remains fused without traditional "tamponade". This validates the principle of the present invention. The gap in the retina on the left hand edge of that illustration is a preparation artefact due to the tissue processing to fix the tissues and make the slides. The separation is in the inner retina not the retina from the RPE.

Discussion

Traditionally, Rhegmatogenous Retinal Detachment (RRD) repair relies on "wound healing" as an active process, over weeks, binding the retina adjacent to the tear to the adjacent RPE. A critical issue is that, because the embryology of the eye involves invagination of the optic cup, there is a potential space between the neurosensory retina and the pigment epithelium and no bridging connective tissue between the retina and RPE. This potential space is lined by the pigment epithelium on one side and the photoreceptor outer segments on the other. These cellular layers are bounded by the retinal outer limiting membrane (OLM) and Bruch's membrane (BM) as parallel basement membranes with no mechanical bridge. Retinal attachment is maintained by multiple factors, in particular, dehydration of the subretinal space by the pigment epithelial pumping action and choroidal oncotic "suction" (Marmor) together with the interphotoreceptor binding protein. Effective retinal detachment repair relies on the formation of a watertight plug between these layers. Traditionally this is accomplished by the formation of connective (granulation) tissue bridging the basement membranes BM and the OLM.

An alternative approach to retinal detachment repair is the inventor's novel concept of direct thermal fusion of two tissue layers: the RPE and the neurosensory retina. Direct fusion is not possible unless the two layers are in contact. During traditional retinal detachment repair, subretinal fluid can be partially drained through a retinotomy, for example, but a thin layer of fluid must remain until the RPE can "pump" the subretinal space "dry". Retinal rotation/translocation is possible due to this persistent fluid as is "retina slippage" during fluid gas exchange. Both the RPE and retinal cells are bounded by their lipid-based cellular membranes and these are hydrophilic (water and fat are not miscible and, in effect, repel each other). Removal of this fluid layer should allow tissue contact and direct fusion to occur. This is similar to placing two eggs in water: if they are separate, heating the water will induce coagulation of both (starting at the boundary) with no fusion/bonding being possible once the surface is coagulated. If the egg white, or mixture of egg white and yolk, is touching, heating the water creates one fused, coagulated and integrated unit.

If there is subretinal fluid between the outer retina and the RPE, laser energy will heat the choroid and RPE and then heat the adjacent "subretinal" fluid which will coagulate or "poach" the outer retina with propagated heat; but if the retina and RPE are not in contact no fusion of the two lipoprotein tissue units is possible. In fact, as in poaching eggs, once the boundary is coagulated no bonding is possible without inflammation forming a coagulum. This study has demonstrated histologically that fusion is possible and has confirmed that in the adjacent area with persistent subretinal fluid, the retina and underlying pigment epithelium/choroid and sclera show acute thermal reaction, but there is no fusion.

The concept of retinal thermofusion is based, in part, on years of laboratory research and clinical observation, many of which have either been published or presented in academic meetings examining the detrimental effect and therapeutic possibilities of manipulating the presence (or absence) of (subretinal) fluid in the subretinal space. The work of Vicente Martinez-Castillo, who performs vitrectomy without post-operative tamponade for retinal detachment repair, has shown that retinal detachment without tamponade is possible.

From clinical observations of the Martinez-Castillo technique, the inventor realised that basic pathological principles could be proactively utilized to achieve reliable retinal and RPE fusion by utilising a novel surgical technique, rather than trying to minimize the detrimental effects of residual fluid alone.

Clinical observation of intraoperative laser reactions in areas with persistent SRF shows either no thermal retinal reaction or bubbles forming in the subretinal space from "steam" due to the intense laser uptake by the choroidal pigment and RPE boiling the subretinal fluid. These phenomenae highlight the negative effect of SRF on effective laser reaction development in both the RPE and the retina. The present inventor is the first to recognize the concept that the water is a physical barrier preventing retina and RPE contact and thus preventing a contiguous thermal reaction, which is the critical issue preventing instant fusion and forcing dependence upon the slower wound healing reaction for retinal detachment repair.

The technique developed by the present inventor involves deliberate desiccation of the subretinal space by: 1. Removing surface vitreous; 2. performing a traditional fluid gas exchange and aspiration of the subretinal fluid through the retinal break; 3. Deliberately drying the retinal tear margin to achieve dehydration of the retina and, indirectly, but most importantly, the subretinal space; and optionally, 4. Applying thermal energy to heat the tissues that are now in contact and achieve fusion of the retina with the pigment epithelium.

The new integrated retina/RPE fused entity eliminates the subretinal space and seals entry of vitreous fluid into the subretinal space. That is, the primary goal of retinal detachment repair: elimination of the subretinal space thus preventing communication between the vitreous cavity fluid and the subretinal space (to produce the retinal detachment). Fusion of both layers immediately corrects the primary pathogenetic factor in rhegmatogenous retinal detachment.

Conclusion:

Removal of residual subretinal fluid creates direct contact between photoreceptors and RPE and allows thermal fusion to create a new merged entity sealing the subretinal space. Direct fusion of the retina and RPE margins of a retinal tear can be achieved by removing the intervening subretinal fluid. Sealing the tear margins should prevent further fluid entering the subretinal space to maintain retinal detachment.

Example 2

Thermofusion will be tested in donor eyes. Human donor eyes from the eye bank or animal eyes such as, pig or cow eyes from an abattoir will be used.

From the freshly dead eye, the vitreous body will be removed and the retinal surface dried to remove excess fluid. The subretinal fluid that accumulates post-mortem separating the retina from the RPE will then be eliminated using the device of the invention.

Thermofusion as outlined herein will then be used to fuse the retina and RPE. Because thermofusion is not healing dependant it does not matter if the animal is not alive. Successful fusion post-mortem would unequivocally establish the utility of thermofusion.

While not wanting to be bound by any one theory, the inventor's hypothesis that a ring of fusion should seal an area of retina so that injecting fluid into the space through a fine needle (41 g used for surgery) could be used to establish the separation force needed to break the fusion caused. An alternative method of measuring the adhesion would be to glue a suture onto the retina and use a micro-strain gauge to measure the adhesion.

The present invention is of significant advantage because it minimizes or eliminates any detrimental inflammatory response following treatment of retinal detachment. Conventionally, the proliferation of RPE and other cells to form surface and intraretinal scar tissue leads to a 5-7% re-detachment rate. The present invention advantageously stops the cell migration from the subretinal space associated with the inflammatory response and may reduce the re-detachment rate. It should also advantageously reduce the risk of post-operative surface scarring that can distort the macula (epiretinal membrane formation and macular pucker) and reduce visual acuity and induce image distortion.

While the invention substantially minimizes or eliminates any detrimental inflammatory response, it is hypothesized that there will be an inflammatory reaction following the treatment as a delayed secondary reaction, but it is not needed for the fusing of the two or more tissues. A mild post-operative inflammatory reaction will augment the seal effect over time in a positive way, making a stronger bond, but the technique of the invention should minimize any detrimental effect of inflammation Other advantages of the present invention include that direct fusion seals the break and therefore prevents re-detachment due to incomplete wound (RPE/retinal) healing. Accordingly, success rates should be significantly improved over the success rate published by most centers using contemporary techniques. The present invention is also much simpler than conventional approaches.

Throughout the specification, the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

Gonin J. La pathogenie du decollement spontane de la retine Ann d'Ocullist (Paris) 132:30 1904

Gonin reported his first surgical successes treating/sealing retinal tears in 1919 (Rumf, J. Jules Gonin. Inventor of the surgical treatment for retinal detachment. Surv. Ophthalmol. 21: 276. 1976) his method consisted of localisation of the retinal tear, scleral puncture and inflammation using a Thermo cautery with a metal probe heated until it was white hot. This was plunged Retinal Detachment. Michels, Wilkinson and Rice. C V Mosby. 1990. Chapter 5 pp: 243-313. History of retinal detachment surgery.

Pars plana vitrectomy, laser retinopexy, and aqueous tamponade for pseudophakic rhegmatogenous retinal detachment. Martinez-Castillo V, Zapata M A, Boixadera A, Fonollosa A, Garcia-Arumi J. Ophthalmology. 2007 February; 114(2):297-302.

Vitrectomy. Machemer, R and Aaberg T M. Grune & Stratton, N.Y. Second edition. 1979. Ch. 12. Practice vitrectomy. P195-207.

The rabbit in cataract/IOL surgery. Arlene Gwon. Animal models in eye research. Animal models in eye research. 2008 Elsevier Ltd.

Ophthalmic lasers. Francis A. L'Esperance, Jr. C V Mosby 1989 Third edition. Vol 1 Ch. 7 P 216.

Eye (1990) 4, 340-344; doi: 10.1038/eye.1990.46; Control of subretinal fluid: Experimental and clinical studies; M F Marmor.

Slippage of the Retina: What Causes It and How Can It Be Prevented?, David Wong. Essentials in ophthalmology; Vitreoretinal surgery. Springer. 2007 DOI 10.1007/978-3-540-33670-9_4. Print ISBN 978-3-540-33669-3; p 41-51.

The rabbit in cataract/IOL surgery. Arlene Gwon. Animal models in eye research. Animal models in eye research. 2008 Elsevier Ltd.

What is claimed is:

1. A device for fusing two or more tissues and treating retinal detachment, the device comprising:
   a hand held probe comprising a fluid receiving opening, a channel and a fluid outlet in fluid communication whereby fluid received in the opening passes through the channel and exits the outlet where it is directed to at least one of the two or more tissues and/or a space in-between to dehydrate at least one of the two or more tissues and/or the space in-between, wherein the two or more tissues comprise the retina and the retinal pigmented epithelium; and
   a laser comprised on the hand held probe which emits a laser light to be directed to at least one of the two or more tissues to fuse the two or more tissues.

2. The device according to claim 1, further comprising a heating element disposed inside the channel for heating the fluid so that fluid exiting the outlet comprises a temperature sufficient to dry the two or more tissues.

3. The device according to claim 2, wherein the heating element is located at a proximal end of the probe to minimise any offset in temperature before fluid exits the outlet.

4. The device according to claim 2 wherein the heating element is controlled by a feedback controller to maintain the heating element at a desired temperature.

5. The device according to claim 1, wherein the laser heats the tissue to a temperature in the range of 70 to 100° C. to thermally fuse the two or more tissues.

6. The device according to claim 1 wherein the laser comprises a blind tip of a laser fibre.

7. The device according to claim 1 wherein the device is for treating or when used to treat a detached retina and/or the probe is an intraocular probe.

* * * * *